(12) United States Patent
Okumura et al.

(10) Patent No.: US 8,211,472 B2
(45) Date of Patent: Jul. 3, 2012

(54) SUSPENSION OF ASCORBIC ACID IN GLYCERIN AND PROCESS FOR PRODUCTION THEREOF

(75) Inventors: Mikiharu Okumura, Tokyo (JP); Takanori Ohta, Tokyo (JP)

(73) Assignee: Market Styles Co., Ltd., Tokyo (JP)

( * ) Notice: Subject to any disclaimer, the term of this patent is extended or adjusted under 35 U.S.C. 154(b) by 306 days.

(21) Appl. No.: 12/445,775

(22) PCT Filed: Oct. 18, 2007

(86) PCT No.: PCT/JP2007/070379
§ 371 (c)(1),
(2), (4) Date: Apr. 16, 2009

(87) PCT Pub. No.: WO2008/050676
PCT Pub. Date: May 2, 2008

(65) Prior Publication Data
US 2011/0008445 A1    Jan. 13, 2011

(30) Foreign Application Priority Data
Oct. 23, 2006  (JP) ................................. 2006-287372

(51) Int. Cl.
*A61K 8/02*   (2006.01)
*A61K 9/14*   (2006.01)

(52) U.S. Cl. ........................................ 424/489; 424/401

(58) Field of Classification Search ........................ None
See application file for complete search history.

(56) References Cited

U.S. PATENT DOCUMENTS

| | | | |
|---|---|---|---|
| 4,829,092 A * | 5/1989 | Nelson et al. | 514/738 |
| 5,308,621 A * | 5/1994 | Taylor et al. | 424/401 |
| 6,224,888 B1 | 5/2001 | Vatter et al. | |
| 6,528,071 B2 | 3/2003 | Vatter et al. | |
| 2001/0033850 A1 | 10/2001 | Vatter et al. | |

FOREIGN PATENT DOCUMENTS

| | | |
|---|---|---|
| JP | 2002-241280 A | 8/2002 |
| JP | 2002536390 A * | 10/2002 |
| JP | 2004-155733 A | 6/2004 |
| JP | 2006-096707 A | 4/2006 |
| WO | WO-00/47170 A1 | 8/2000 |

* cited by examiner

*Primary Examiner* — Robert A Wax
*Assistant Examiner* — Olga V Tcherkasskaya
(74) *Attorney, Agent, or Firm* — Oblon, Spivak, McClelland, Maier & Neustadt, L.L.P.

(57) ABSTRACT

A suspension of ascorbic acid in glycerol or in glycerol comprising diglycerol, in which the content of ascorbic acid is 13% by mass or greater, and further in which 8 to 12% by mass of the ascorbic acid is dissolved in glycerol or in glycerol comprising diglycerol, and the rest of ascorbic acid is precipitated in the form of microcrystals having a particle diameter of 25 μm or smaller and is uniformly dispersed in the suspension. The suspension of ascorbic acid in glycerol is useful as a base material for cosmetics containing ascorbic acid which exhibits excellent feel in the use (spreadability and smooth feel on application to the skin).

9 Claims, 6 Drawing Sheets

[Fig 1]
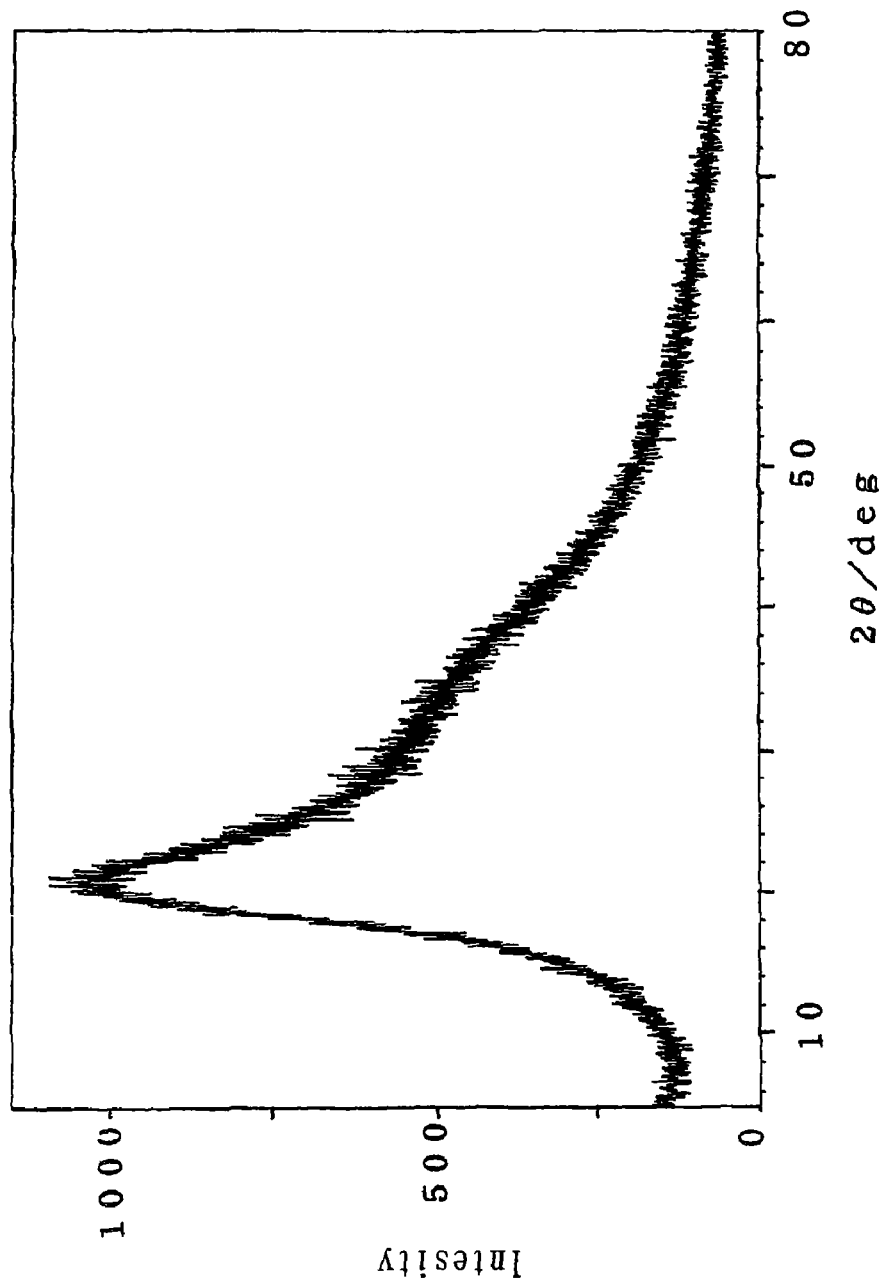

[Fig 2]
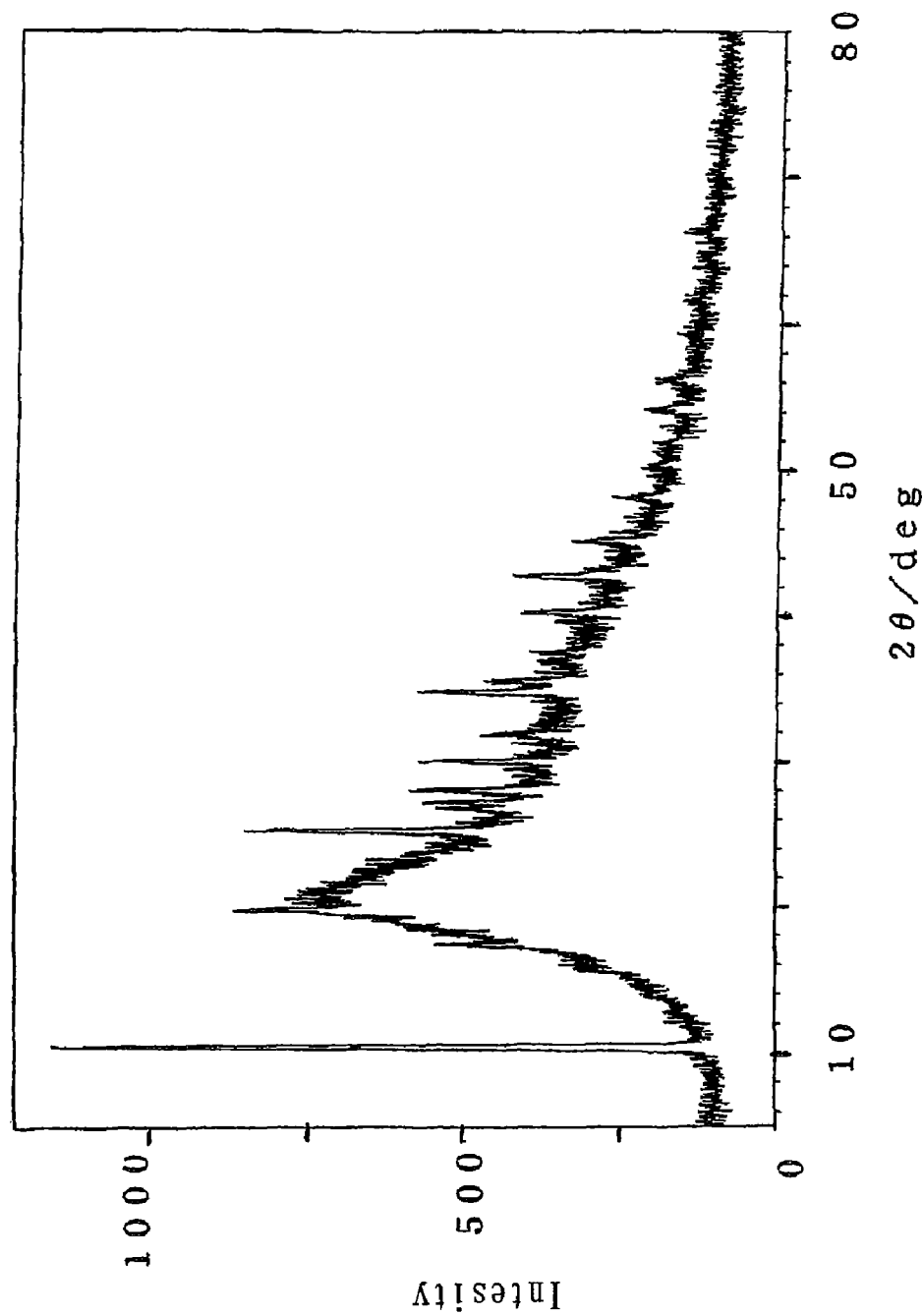

[Fig 3]
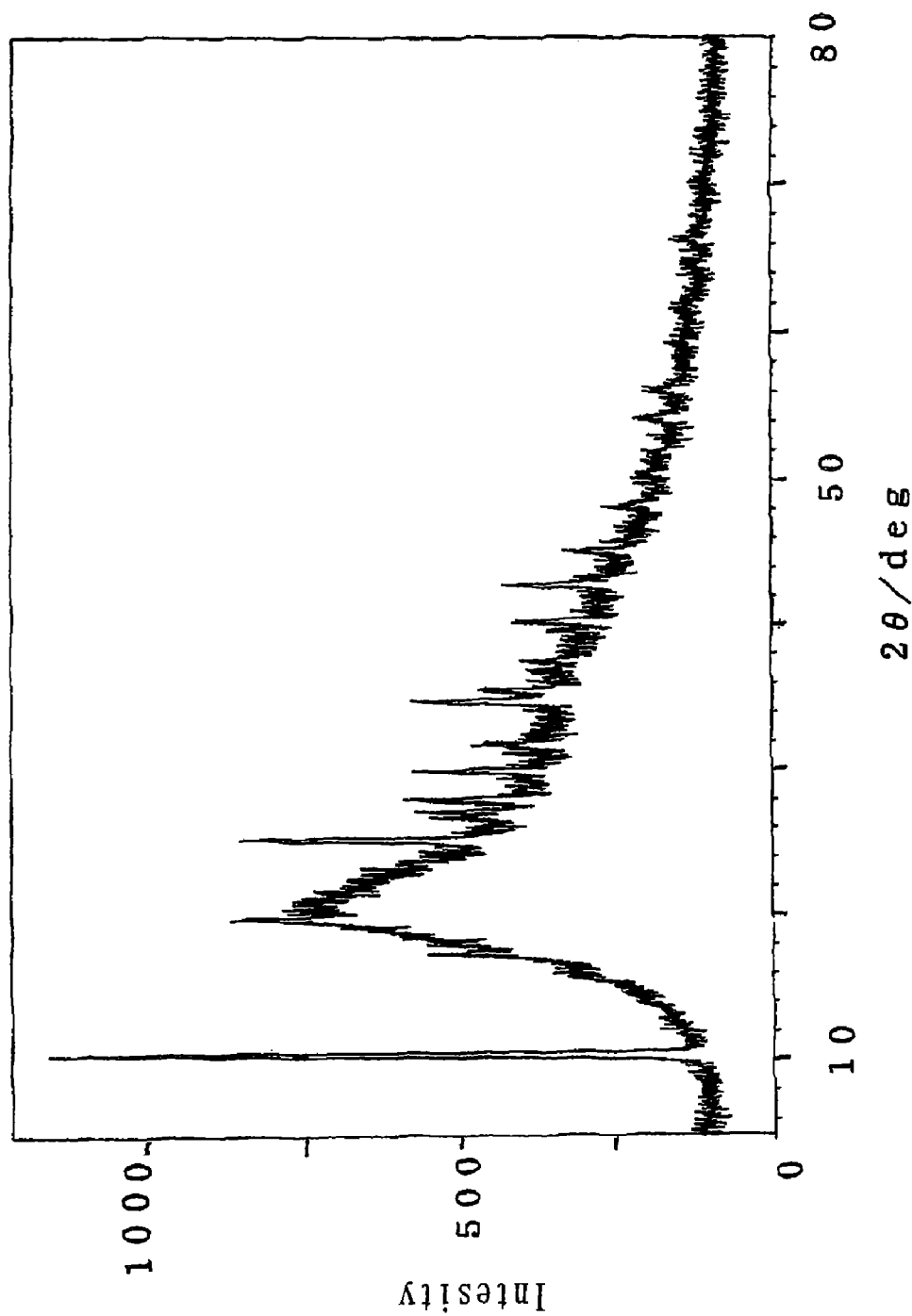

[Fig 4]
—— 20 μm

[Fig 5]
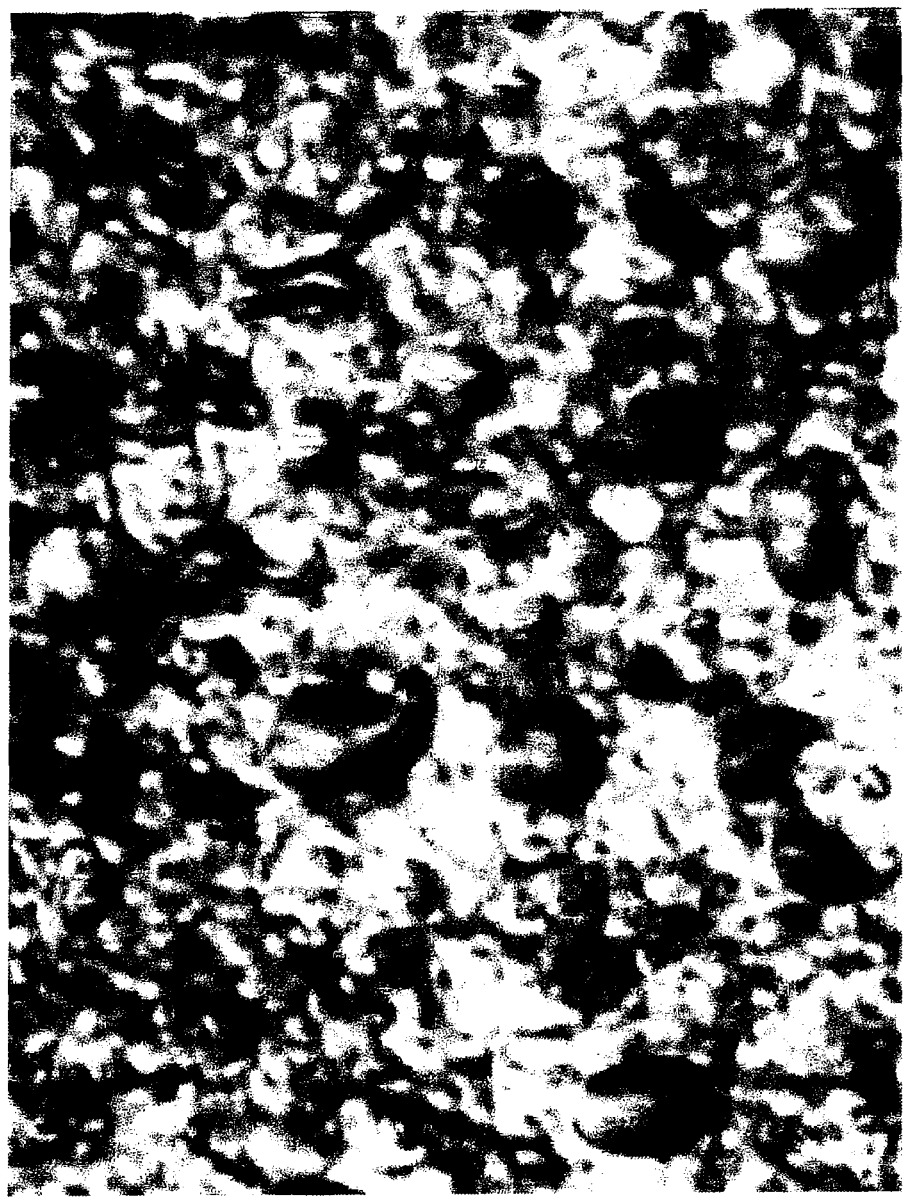

[Fig 6]

SUSPENSION OF ASCORBIC ACID IN GLYCERIN AND PROCESS FOR PRODUCTION THEREOF

CROSS REFERENCE TO PRIOR RELATED APPLICATIONS

This application is a U.S. National Phase Application under 35 U.S.C. §371 of International Patent Application No. PCT/JP2007/070379, filed on Oct. 18, 2007, and claims the benefit of Japanese Patent Application No. 2006-287372, filed on Oct. 23, 2006, both of which are incorporated by reference herein. The International Application was published in Japanese on May 2, 2008, as International Publication No. WO 2008/050676 A1 under PCT Article 21(2).

TECHNICAL FIELD

The present invention relates to a suspension of ascorbic acid in glycerin (hereinafter, glycerin will be referred to as glycerol and, occasionally, a suspension in glycerin will be referred to as a glycerol suspension) in which the content of ascorbic acid is 13% by mass or greater, in which 8 to 12% by mass of the ascorbic acid is dissolved in glycerol or glycerol comprising diglycerol, and the rest of ascorbic acid is precipitated in the form of microcrystals having a particle diameter of 25 μm or smaller and is uniformly dispersed in the suspension and a process for producing the suspension.

BACKGROUND ART

Ascorbic acid exhibits the effect of preventing aging of skin since ascorbic acid exhibits the function of antioxidation and takes part in forming and maintaining collagen. Therefore, ascorbic acid is used for skin whitening products as a component for preventing formation of spots and freckles, i.e., a safe raw material for skin whitening.

Ascorbic acid is used also as a drug for supplementing vitamin C and a drug for curing pigmentation, drug intoxication and adrenal cortex dysfunction.

Ascorbic acid is used also in cooling drinks, preserved foods, cookies and healthy foods.

However, when ascorbic acid is dissolved in water, ascorbic acid is very unstable and easily oxidized in the presence of light, heat or metal ions or depending on pH. It is difficult that an aqueous solution of ascorbic acid in a great concentration is stored with stability when such a solution is prepared.

The present inventors considered that the applications described above could be expanded and new applications could be found when a solution of ascorbic acid in an organic solvent which contained ascorbic acid in a great concentration and was stable could be prepared. A process for producing a solution containing 16 to 45% by mass of ascorbic acid in glycerol had been developed, and the patent application was made.

Heretofore, it is known that ascorbic acid can be dissolved in glycerol to the maximum concentration of 15% by mass (refer to Patent Reference 1).

The concentration of ascorbic acid in the glycerol solution obtained in accordance with the above process developed by the present inventors is 16 to 45% by mass.

When the glycerol solution containing ascorbic acid in the concentration as great as that described above is used as the base material for cosmetics, it is desired that the feel in the use (spreadability and smooth feel on application to the skin) of the solution is further improved.

[Patent Reference 1] Japanese Patent Application Laid-Open No. 2004-155733

DISCLOSURE OF THE INVENTION

The present invention has been made to overcome the above problem and has an object of providing a suspension of ascorbic acid in glycerol or glycerol comprising diglycerol, in which the content of ascorbic acid is 13% by mass or greater, and further in which 8 to 12% by mass of the ascorbic acid is dissolved in glycerol or glycerol comprising diglycerol, and the rest of ascorbic acid is precipitated in the form of microcrystals having a particle diameter of 25 μm or smaller and is uniformly dispersed in the suspension and a process for producing the suspension.

As the result of intensive studies by the present inventors to achieve the above object, it was found that a white suspension of ascorbic acid in glycerol obtained by precipitating a portion of ascorbic acid in a solution in glycerol or in glycerol containing diglycerol containing ascorbic acid in a great concentration in the form of microcrystals having a particle diameter of 25 μm or smaller and uniformly dispersing the formed precipitates in the suspension exhibited excellent feel in the use.

The present invention has been completed based on the above knowledge.

The present invention provides:

1. A suspension of ascorbic acid in glycerol in which a content of ascorbic acid is 13% by mass or greater, wherein 8 to 12% by mass of the ascorbic acid is dissolved in glycerol or in glycerol comprising diglycerol, and rest of ascorbic acid is precipitated in a form of microcrystals having a particle of 25 μm or smaller and is uniformly dispersed in the suspension;
2. A suspension of ascorbic acid in glycerol described in 1., above, wherein the content of ascorbic acid is 16 to 45% by mass;
3. A suspension of ascorbic acid in glycerol described in any one of 1. and 2., above, wherein a content of diglycerol in glycerol comprising diglycerol is 0.1 to 10% by mass;
4. A process for producing a suspension of ascorbic acid in glycerol described in 1., above, which comprises mixing ascorbic acid, glycerol or glycerol comprising diglycerol, and ethyl alcohol, dissolving the ascorbic acid in the obtained mixture, removing ethyl alcohol from the mixture, and aging the obtained solution of ascorbic acid in glycerol at 20° C. to 40° C. for at least 3 days, wherein the ascorbic acid solution comprises 13% by mass or greater of ascorbic acid;
5. A process for producing a suspension of ascorbic acid in glycerol described in 4., above, wherein a content of ascorbic acid is 16 to 45% by mass; and
6. A process for producing a suspension of ascorbic acid in glycerol as described in any one of 4. and 5., above, wherein a content of diglycerol in glycerol comprising diglycerol is 0.1 to 10% by mass.

The suspension of ascorbic acid in glycerol of the present invention, in which a portion of ascorbic acid is dissolved in glycerol or glycerol comprising diglycerol in a concentration of 8 to 12% by mass, and the rest of ascorbic acid is precipitated in the form of microcrystals having a particle diameter of 25 μm or smaller and is uniformly dispersed in the suspension, exhibits more excellent feel in the use as the base material for cosmetics than that exhibited with a solution of ascorbic acid in glycerol containing ascorbic acid in a great concentration.

The suspension of ascorbic acid in glycerol of the present invention is stable for a long time at 25° C. or lower and can be used immediately for desired applications.

BRIEF DESCRIPTION OF THE DRAWINGS

FIG. 1 shows a diagram exhibiting an X-ray diffraction pattern of Glycerol solution of ascorbic acid 2 in Example 2.

FIG. 2 shows a diagram exhibiting an X-ray diffraction pattern of Glycerol suspension of ascorbic acid 2a in Example 2.

FIG. 3 shows a diagram exhibiting an X-ray diffraction pattern of crystals of ascorbic acid.

FIG. 4 shows a diagram exhibiting an optical microscopic picture [500 times magnification] of Glycerol suspension of ascorbic acid 2a in Example 2.

FIG. 5 shows a diagram exhibiting an optical microscopic picture [500 times magnification] of Glycerol suspension of ascorbic acid 2b in Example 2.

FIG. 6 shows a diagram exhibiting an optical microscopic picture [500 times magnification] of crystals of ascorbic acid.

THE MOST PREFERRED EMBODIMENT TO CARRY OUT THE INVENTION

The present invention will be described more specifically in the following.

The present invention relates to a white suspension of ascorbic acid in glycerol or glycerol comprising diglycerol, in which the content of ascorbic acid is 13% by mass or greater, and further in which 8 to 12% by mass of the ascorbic acid is dissolved in glycerol or in glycerol comprising diglycerol, and the rest of ascorbic acid is precipitated in the form of microcrystals having a particle diameter of 25 μm or smaller and is uniformly dispersed in the suspension and a process for producing the suspension.

In the suspension of ascorbic acid in glycerol of the present invention, the content of ascorbic acid is, in general, 13 to 45% by mass.

It is preferable that the content of ascorbic acid is 16 to 45% by mass, more preferably 16 to 40% by mass and most preferably 20 to 35% by mass.

As for the amount of ascorbic acid dissolved in glycerol or glycerol comprising diglycerol in the suspension of ascorbic acid in glycerol of the present invention, ascorbic acid is dissolved in glycerol or glycerol comprising diglycerol, in general, in a concentration of 8 to 12% by mass, and the rest of ascorbic acid is precipitated.

It is preferable that ascorbic acid is dissolved in glycerol or glycerol comprising diglycerol in a concentration of 9 to 11% by mass.

The content of diglycerol in glycerol comprising diglycerol is, in general, 10% by mass or smaller, preferably 0.1 to 7% by mass and more preferably 0.5 to 5% by mass.

When the content of diglycerol is within the above range, the spreadability is improved and viscous feel tends to be formed slightly in comparison with those obtained by using glycerol alone, and these feels in the use of the cosmetic can be adjusted in accordance with the object.

The diameter (the maximum diameter) of the microcrystals of the precipitates of ascorbic acid is, in general, 25 μm or smaller.

When the diameter (the maximum diameter) of the microcrystals of the precipitates of ascorbic acid is 25 μm or smaller, the feel in the use as the base material for cosmetics is excellent.

The suspension of ascorbic acid in glycerol of the present invention can be produced by mixing ascorbic acid, glycerol or glycerol comprising diglycerol, and ethyl alcohol, dissolving the ascorbic acid in the obtained mixture, removing ethyl alcohol from the mixture, and aging the obtained solution of ascorbic acid in glycerol at 20° C. to 40° C. for at least 3 days, wherein the ascorbic acid solution comprises 13% by mass or greater of ascorbic acid.

The process for producing the solution of ascorbic acid in glycerol or glycerol comprising diglycerol having a content of ascorbic acid of 13% by mass or greater will be described in the following.

The process for producing the solution of ascorbic acid in glycerol or glycerol comprising diglycerol is not particularly limited. For example, the above solution can be produced by mixing ascorbic acid, glycerol or glycerol comprising diglycerol and ethyl alcohol to dissolve ascorbic acid in the obtained mixture using ethyl alcohol as the auxiliary agent for dissolving ascorbic acid, followed by removing ethyl alcohol from the mixture.

The content of diglycerol in glycerol comprising diglycerol is, in general, 10% by mass or smaller, preferably 0.1 to 7% by mass and more preferably 0.5 to 5% by mass.

Ascorbic acid is a white odorless crystalline or powder substance expressed by the formula $C_6H_8O_6$ having a molecular weight of 176.13 and is relatively stable in the form of crystals or powder.

However, ascorbic acid becomes very unstable and easily oxidized when ascorbic acid is dissolved in water.

Glycerol is a colorless, transparent and viscous liquid substance (1499 mPa·s at 20° C.).

The toxicity of glycerol is small, and glycerol is frequently used as the base material for cosmetics.

Diglycerol is a viscous liquid substance obtained by condensation with dehydration of two molecules of glycerol. Similarly to glycerol, the toxicity of diglycerol is small, and diglycerol is frequently used as the base material for cosmetics.

Ethyl alcohol is a colorless transparent liquid substance having specific odor and taste. Ethyl alcohol can be mixed with ascorbic acid in any desired relative amounts to form a homogeneous solution.

The amount of ethyl alcohol is not particularly limited and different depending on the desired concentration of ascorbic acid and the temperature of dissolution by heating. In general, the amount of ethyl alcohol is 40 to 60 parts by mass and preferably 45 to 50 parts by mass per 1 part by mass of ascorbic acid.

For mixing ascorbic acid, glycerol or glycerol comprising diglycerol and ethyl alcohol, the entire necessary amounts of these components may be mixed at once or these components may be mixed in small portions consecutively.

The order of mixing ascorbic acid, glycerol or glycerol comprising diglycerol and ethyl alcohol is not particularly limited. It is preferable that ethyl alcohol is mixed into a mixture of ascorbic acid and glycerol or glycerol comprising diglycerol since the rate of dissolution of ascorbic acid is increased.

From the standpoint of the rate of dissolution, it is preferable that stirring is conducted when ascorbic acid, glycerol or glycerol comprising diglycerol and ethyl alcohol are mixed to dissolve ascorbic acid in the obtained mixture.

Where necessary, heating may be conducted when ascorbic acid, glycerol or glycerol comprising diglycerol and ethyl alcohol are mixed to dissolve ascorbic acid in the obtained mixture.

It is preferable that, when ascorbic acid is dissolved, the dissolution is conducted while the mixture of ascorbic acid, glycerol or glycerol comprising diglycerol and ethyl alcohol is heated under stirring in a vessel equipped with a stirrer.

The temperature of heating is, in general, 15 to 60° C., preferably 15 to 50° C. and more preferably 20 to 40° C.

Where necessary, the operation of dissolution may be conducted under a stream of an inert gas such as nitrogen gas.

The solution comprising ascorbic acid, glycerol or glycerol comprising diglycerol and ethyl alcohol obtained as described above is a colorless transparent solution.

Then, ethyl alcohol is removed from the obtained solution comprising ascorbic acid, glycerol or glycerol comprising diglycerol and ethyl alcohol.

As the process for removing ethyl alcohol, in general, the distillation process is used.

The solution of ascorbic acid in glycerol comprising 13% by mass or greater of ascorbic acid can be easily obtained as described above.

The suspension of ascorbic acid in glycerol of the present invention can be produced by aging the solution of ascorbic acid in glycerol comprising 13% by mass or greater of ascorbic acid obtained as described above, in general, at a temperature of 20 to 40° C. for 3 days or longer (the aging means keeping the solution at a temperature of 20 to 40° C.).

When the temperature and the time of the aging is within the above range, ascorbic acid is precipitated in the form of microcrystals having a diameter of 25 μm or smaller and is dispersed uniformly in the obtained suspension of ascorbic acid in glycerol, and the suspension exhibits the excellent feel in the use when the suspension is used as the base material for cosmetics.

The time of the aging described above means the period of time required for the amount of the microcrystals of ascorbic acid formed by the precipitation and suspended in the solution of ascorbic acid in glycerol to become constant.

Therefore, the suspension of ascorbic acid of the present invention obtained as described above is stable and causes no problems when the suspension is left standing under the condition of the aging for a time longer than the time of aging.

The temperature of the aging is 20 to 40° C. and preferably 28 to 32° C.

The time of the aging (the period of time being left standing) is varied depending on the content of ascorbic acid in the obtained solution of ascorbic acid in glycerol.

In general, the suspension of ascorbic acid in glycerol exhibiting excellent properties can be produced in a relatively shorter time of the aging when the content of ascorbic acid is greater.

In other words, when the content of ascorbic acid in the solution is smaller, the suspension of ascorbic acid in glycerol exhibiting excellent properties can be produced by aging for a relatively longer time.

For example, when the content of ascorbic acid is 22 to 45% by mass, the time of the aging is, in general, 3 days or longer, preferably 5 days or longer and more preferably 10 days or longer.

When the content of ascorbic acid is 13% by mass or greater and smaller than 22% by mass, the time of the aging is, in general, 10 days or longer, preferably 15 days or longer and more preferably 20 days or longer.

The suspension of ascorbic acid in glycerol of the present invention is stable for a long time without degradation in the quality at 25° C. or lower and can be used immediately for desired applications.

The container for storing the suspension of ascorbic acid in glycerol is not particularly limited as long as the material for the container is inert to ascorbic acid and glycerol and is durable at the temperature of storage.

Examples of the container include containers made of glass or plastics.

EXAMPLES

The present invention will be described more specifically with reference to examples in the following. However, the present invention is not limited to the examples.

Example 1

Ascorbic acid in an amount of 10 g, 40 g of glycerol and 380 g of ethyl alcohol were weighed and placed into a flask. When the obtained mixture was stirred at 25° C. for 15 minutes, ascorbic acid was dissolved completely.

When ethyl alcohol was removed at a temperature of 25° C. under a pressure of 0.67 kPa (5 mmHg) over 1.5 hours, a transparent solution of ascorbic acid in glycerol was obtained ("Glycerol solution of ascorbic acid 1").

The obtained solution of ascorbic acid in glycerol was analyzed with respect to ascorbic acid in accordance with the high performance liquid chromatography, and the content of ascorbic acid was found to be 20.1% by mass.

The turbidity of the obtained solution of ascorbic acid in glycerol was measured in accordance with the method of measuring scattered light of Japanese Industrial Standard K0101 using formazine as the reference substance and was found to be 5 or smaller.

After Glycerol solution of ascorbic acid 1 obtained as described above was placed into a container and kept in a thermostatic room at a temperature of aging of 28° C. for a time of aging of 10 days while the upper space of the container was not filled with an inert gas such as nitrogen, white Glycerol suspension of ascorbic acid 1a in which the concentration of ascorbic acid in the glycerol solution was 9.8% by mass and the rest of ascorbic acid was precipitated in the form of microcrystals and uniformly dispersed was obtained ("Glycerol suspension of ascorbic acid 1a").

Separately, after the above solution was kept in a thermostatic room at a temperature of aging of 15° C. for a time of aging of 15 days, Glycerol suspension of ascorbic acid 1b in which the concentration of ascorbic acid in the glycerol solution was 9.2% by mass and the rest of ascorbic acid was precipitated in the form of crystals was obtained ("Glycerol suspension of ascorbic acid 1b").

Glycerol solution of ascorbic acid 1 and Glycerol suspensions of ascorbic acid 1a and 1b in Example 1 obtained above were examined by the measurement of X-ray diffraction, and it was found that crystals of ascorbic acid were present in Glycerol suspensions of ascorbic acid 1a and 1b.

Glycerol suspensions of ascorbic acid 1a and 1b were examined by observation using an optical microscope (500 times magnification). It was found that the maximum diameter (the length of the major axis) of the microcrystals of ascorbic acid precipitated in Glycerol suspension of ascorbic acid 1a was 25 μm or smaller, and the maximum diameter of the microcrystals of ascorbic acid precipitated in Glycerol suspension of ascorbic acid 1b exceeded 80 μm.

Almost the entire crystals in Glycerol suspension of ascorbic acid 1a had long shapes having a length of the minor axis of about 5 μm. In contrast, in crystals in Glycerol suspension of ascorbic acid 1b, many particles having major axes and minor axes which were about the same and exceeded 40 μm were contained in a great amount.

Example 2

Ascorbic acid in an amount of 14 g, 25 g of glycerol and 380 g of ethyl alcohol were weighed and placed into a flask. When the obtained mixture was stirred at 25° C. for 15 minutes, ascorbic acid was dissolved completely.

When ethyl alcohol was removed at a temperature of 25° C. under a pressure of 0.67 kPa (5 mmHg) over 2 hours, a transparent solution of ascorbic acid in glycerol was obtained ("Glycerol solution of ascorbic acid 2").

The obtained solution of ascorbic acid in glycerol was analyzed with respect to ascorbic acid in accordance with the high performance liquid chromatography, and the content of ascorbic acid was found to be 35.2% by mass.

The turbidity of the obtained solution of ascorbic acid in glycerol was measured in accordance with the same method as that conducted in Example 1 and was found to be 5 or smaller.

After Glycerol solution of ascorbic acid 2 obtained as described above was placed into a container and kept in a thermostatic room at a temperature of aging of 31° C. for a time of aging of 7 days while the upper space of the container was not filled with an inert gas such as nitrogen, white Glycerol suspension of ascorbic acid 2a in which the concentration of ascorbic acid in the glycerol solution was 10.3% by mass and the rest of ascorbic acid was precipitated in the form of microcrystals and uniformly dispersed was obtained ("Glycerol suspension of ascorbic acid 2a").

Separately, after the above solution was kept in a thermostatic room at a temperature of aging of 15° C. for a time of aging of 15 days, Glycerol suspension of ascorbic acid 2b in which the concentration of ascorbic acid in the glycerol solution was 10.1% by mass and the rest of ascorbic acid was precipitated in the form of crystals was obtained ("Glycerol suspension of ascorbic acid 2b").

Glycerol solution of ascorbic acid 2, Glycerol suspension of ascorbic acid 2a and crystals of ascorbic acid in Example 2 obtained above were examined by the measurement of X-ray diffraction using an apparatus for X-ray diffraction measurement (X-ray; CuK a1; λ; 1.5406), and it was found that crystals of ascorbic acid were present in Glycerol suspension of ascorbic acid 2a and were absent in Glycerol solution of ascorbic acid 2.

The results are shown in FIGS. 1, 2 and 3.

Glycerol suspensions of ascorbic acid 2a and 2b were examined by observation using an optical microscope (500 times magnification). It was found that the maximum diameter (the length of the major axis) of the microcrystals of ascorbic acid precipitated in Glycerol suspension of ascorbic acid 2a was 25 μm or smaller, and the maximum diameter of the microcrystals of ascorbic acid precipitated in Glycerol suspension of ascorbic acid 2b exceeded 80 μm.

Crystals of ascorbic acid were examined by observation using an optical microscope (500 times magnification).

The results are shown in FIGS. 4, 5 and 6.

(Evaluation 1)

The feel in the use on application of Glycerol solutions of ascorbic acid 1 and 2 and Glycerol suspensions of ascorbic acid 1a, 2a, 1b and 2b obtained in Examples 1 and 2 to the skin was evaluated by 10 monitors and classified into the following three grades. The results shown in Table 1 were obtained.

TABLE 1

|  |  | Feel in the use |
|---|---|---|
| Example 1 | Glycerol solution of ascorbic acid 1 | fair |
|  | Glycerol suspension of ascorbic acid 1a | good |
|  | Glycerol suspension of ascorbic acid 1b | poor |
| Example 2 | Glycerol solution of ascorbic acid 2 | fair |
|  | Glycerol suspension of ascorbic acid 2a | good |
|  | Glycerol suspension of ascorbic acid 2b | poor | good: excellent spreadability and smooth feel on application to the skin; excellent feel in the use
fair: feel in the use somewhat inferior to the above
poor: rough feel on application to the skin; poor feel in the use (Evaluation 2)

Thirty monitors were requested to apply Glycerol suspension of ascorbic acid 2a obtained in Example 2 to the face, as the general rule, every day for 3 weeks. Eighty percent or more of the monitors reported that at least one of the following effects could be actually felt.

1. Elasticity of the skin was maintained; slacks and wrinkles were prevented or the conditions of slacks and wrinkles were improved.

2. Formation of melanin was suppressed; formation of freckles was prevented or condition of freckles was improved.

3. Excessive secretion of fats from the skin was suppressed to prevent formation of peroxide fats; condition of pimples was improved.

4. Balance among the natural factors maintaining moisture in the horny layers was normalized, and moisture was obtained on the skin.

It is shown by the results in Table 1 that the suspension of ascorbic acid in glycerol of the present invention exhibited the excellent feel in the use and could be used as the base material for cosmetics in various applications.

Example 3

Using 14 g of ascorbic acid, 24.75 g of glycerol, 0.25 g of diglycerol and 380 g of ethyl alcohol, white Glycerol suspension of ascorbic acid 3a in which ascorbic acid in an amount corresponding to that in Glycerol suspension of ascorbic acid 2a in Example 2 was precipitated in the form of microcrystals and uniformly dispersed was obtained in accordance with the same procedures as those conducted in Example 2 ("Glycerol suspension of ascorbic acid 3a").

Ten monitors were requested to apply Glycerol suspension of ascorbic acid 3a obtained above to the skin and evaluate the feel in the use. It was reported that the feel in the use was excellent and the spreadability was improved from that obtained by using glycerol alone although some viscous feel was found.

Industrial Applicability

The suspension of ascorbic acid in glycerol of the present invention, in which a portion of ascorbic acid is dissolved in glycerol or glycerol comprising diglycerol in a concentration of 8 to 12% by mass, and the rest of ascorbic acid is precipitated in a form of microcrystals having a particle diameter of 25 μm or smaller and is uniformly dispersed in the suspension, exhibited more excellent feel in the use as the base material for cosmetics, is stable for longer time and can maintain the effect of ascorbic acid with stability in comparison with a solution of ascorbic acid in glycerol containing ascorbic acid in a great concentration. Therefore, cosmetics, drugs and foods containing ascorbic acid in a great amount with stability can be produced.

The invention claimed is:

1. A process for producing a suspension of ascorbic acid in glycerol wherein the suspension comprises ascorbic acid in an amount of 13% by mass or greater; wherein 8 to 12% by mass of the ascorbic acid is dissolved in the glycerol, and the rest of the ascorbic acid is crystallized in a form of microcrystals having a particle diameter of 25 μm or smaller, wherein the ascorbic acid microcrystals are uniformly dispersed in the suspension, the process comprising:
    mixing the ascorbic acid, the glycerol and ethyl alcohol to form a mixture and to dissolve the ascorbic acid in the glycerol and the ethyl alcohol;
    forming the suspension comprising the microcrystals of ascorbic acid and the glycerol by removing the ethyl alcohol from the mixture; and
    aging the microcrystals of ascorbic acid having a particle diameter of 25 μm or smaller in the suspension comprising 13% by mass or greater of the ascorbic acid at 20 to 40° C. for at least 3 days.

2. The process according to claim 1, wherein a content of ascorbic acid in the suspension is 16 to 45% by mass.

3. The process according to claim 1, wherein the step of mixing further comprises adding diglycerol in an amount of 0.1 to 10% by mass.

4. The process according to claim 1, wherein the suspension further comprises diglycerol in an amount of 0.1 to 10% by mass.

5. The process according to claim 1, wherein the amount of the ethyl alcohol in the mixture is 40 to 60 parts by mass per 1 part by mass of the ascorbic acid.

6. The process according to claim 1, wherein the microcrystals have long shapes with a length in the minor axis of about 5 μm.

7. The process according to claim 1, wherein the ascorbic acid is dissolved in the glycerol in an amount of 9 to 11% by mass in the mixture.

8. The process according to claim 1, wherein the ascorbic acid is present in the suspension in an amount of 20 to 35% by mass.

9. The process according to claim 1, wherein the suspension further comprises diglycerol in an amount of 0.5 to 5% by mass.

* * * * *